US005783560A

United States Patent [19]

Gluckman

[11] Patent Number: 5,783,560
[45] Date of Patent: Jul. 21, 1998

[54] USE OF HUMAN GROWTH HORMONE FOR PREOPERATIVE ADMINISTRATION

[75] Inventor: Peter Gluckman, Auckland, New Zealand

[73] Assignee: Pharmacia & Upjohn Aktiebolag, Stockholm, Sweden

[21] Appl. No.: 553,375

[22] PCT Filed: Jun. 16, 1994

[86] PCT No.: PCT/SE94/00596

§ 371 Date: Nov. 27, 1995

§ 102(e) Date: Nov. 27, 1995

[87] PCT Pub. No.: WO95/00167

PCT Pub. Date: Jan. 5, 1995

[30] Foreign Application Priority Data

Jun. 25, 1993 [SE] Sweden ..................... 247990

[51] Int. Cl.⁶ .................. A61K 38/00; A61K 31/195; A61K 31/70; A61K 31/715
[52] U.S. Cl. ......................... 514/12; 530/399
[58] Field of Search ..................... 530/399; 514/12

[56] References Cited

U.S. PATENT DOCUMENTS 5,179,080  1/1993  Rothkopf ..................... 514/12

FOREIGN PATENT DOCUMENTS

WO 87/04074  7/1987  WIPO.
WO 91/11196  8/1991  WIPO.

OTHER PUBLICATIONS

Hollander et al., Increased Wound Breaking Strength in Rats Following Treatment with Synthetic Human Growth Hormone, Surgical Forum, vol. 35 (1984), pp. 612–614.

Zaizen et al., The Effect of Perioperative Exogenous Growth Hormone on Wound Bursting Strength in Normal and Malnourished Rats, Journal of Pediatric Surgery, vol. 25, No. 1 (1990), pp. 70–74.

Jiang et al., Low–Dose Growth Hormone and Hypocaloric Nutrition Attenuate the Protein–Catabolic Response After Major Operation, Ann Surg. vol. 210, No. 4 (1989), pp. 513–525.

Gustafsson, Possible Metabolic Side Effects of High Dose Growth Hormone Treatment, Acta Pediatr. Suppl., vol. 362 (1989), pp. 50–55.

*Primary Examiner*—Cecilia J. Tsang
*Assistant Examiner*—P. Lynn Touzeau
*Attorney, Agent, or Firm*—Pollock, Vande Sande & Priddy

[57] ABSTRACT

The invention relates to the use of growth hormone (GH) or effective analogues thereof for the manufacture of a medicament intended for preoperative administration in order to reduce protein loss, especially for the manufacture of a medicament for the preparation of a patient for surgery or other elective situation where catabolism may be induced.

20 Claims, 2 Drawing Sheets

USE OF HUMAN GROWTH HORMONE FOR PREOPERATIVE ADMINISTRATION

The present invention relates to the use of growth hormone (GH) or effective analogues thereof for the manufacture of a medicament intended for preoperative administration in order to reduce protein loss and for the preparation of patients for surgery so as to achieve an improved outcome.

INTRODUCTION

Growth hormone (GH) is a peptide present in plasma. It is a 191 amino acid peptide secreted into the blood stream. It acts on receptors in the liver, muscle, fat, growth plate and in other tissues. Its actions on skeletal growth and on protein anabolism are mediated at least in large part by insulin-like growth factor-1 (IGF-1). IGF-1 is released by the liver into the blood stream in response to stimulation by GH. It is also produced in tissues including muscle in response to the action of GH. Human GH has been purified from human tissues and the complete amino acid sequences established. GH is found in other species including ruminants with extensive homologies to those in humans. Because GH can only be purified from the human pituitary gland it is scarce: further purified GH is considered unsafe because of the risk of contamination by prions.

Nowadays large scale production for both hormones is readily achieved using recombinant DNA techniques. It has been demonstrated that recombinant GH (rGH) stimulates skeletal growth in GH deficiency and that it reduces protein catabolism in patients with severe catabolic illness consequence on surgery or burns. These effects of GH are due to a reduction in protein breakdown and possibly an increase in protein synthesis. Moreover these actions of GH are associated with a rise in serum IGF-1 levels.

In EP 288 478, Brigham and Women's hospital, the use of growth hormone together with a hypocaloric dietary component is disclosed for producing or maintaning a positive nitrogen balance. The protein builtup is thereby maintained.

WO 91/11195, Novo Nordisk, discloses the use of growth hormone for reducing the incidence of post-surgical problems, wherein the hormone is administered for a period starting at the time of an operation.

However, all consideration of the use of GH to ameliorate a catabolic state has been restricted to its use after a state of catabolism exists. Prior art does not exist to suggest an alternate use or approach or that the use of GH prior to an insult would be of therapeutic value.

THE INVENTION

We have found that a specific biological action of GH and its analogues, when administered to mammals including man for a period prior to the induction of a catabolic state reduces the severity of the catabolic state.

We have also found that prophylactic use of GH or effective analogues acts to allow parenteral nutritional therapy to be effective in a catabolic state in a manner not seen if GH is administered solely after the catabolism has been established. Thus GH or affective analogues are, according to the present invention, suitable preparative therapies for human subjects facing elective surgery or other comparable catabolic stresses.

The use is especially of interest for the preparation of a patient for major surgery of an elective nature including major cardiac surgery, major abdominal surgery, orthopaedic surgery, neurosurgery, or any other surgical procedure of an elective nature. A universal problem of major surgery is that catabolic states develop after surgery which prolong the patients convalescence and increase the risk of death or morbidity from cardiac, respiratory or infective complication and slow the rate of wound healing. The invention discloses the considerable advantage to the patient placed electively in that position if prepared for a period prior to the surgery with GH or its effective analogue to both reduce the severity of the catabolic state and/or improve the capacity of the patient to respond to current therapeutic modalities which are nutritional support and/or GH administration.

The invention thus relates to the use of growth hormone (GH) or effective analogues thereof for the manufacture of a medicament intended for preoperative administration in order to reduce protein loss and thus for improvement in outcome following surgery.

Normally this applies in the preparation of a patient for surgery or other elective situation where catabolism may be induced in order to reduce the severity of a postoperative catabolic state.

It also relates to the use for the manufacture of a medicament for preoperative and postoperative administration for the preparation of a patient for surgery or other elective situation where catabolism may be induced, i.e. that GH is given prior to surgery and thereafter continously after surgery.

The surgery includes abdominal, cardiac, thoracic, neuro or orthopaedic surgery.

Preferably human GH is used and the dose administered could be 0.1 to 1 mg/kg/day preferably 0.1 to 0.4 mg/kg/day.

The invention also relates to the method of treatment of patients in the situations as given above.

The administration of GH could be subcutaneous, intramuscular, intravenous, intranasal, oral or dermal or a combination of these routes. And the hormone is administered for at least 12 hours and up to 365 days and preferably for 3 to 60 days.

This claimed use of GH prior to surgery enhances the efficacy of hormonal, pharmaceutical or nutritional management of a postoperative catabolic state.

The hormone may be used in association with other nutritional, pharmaceutical or hormonal therapies pre- and/ or post surgical.

The capacity of patients to maintain metabolic status during investigations that require the withdrawal of food (for example bowel biopsy, radiological investigation) could be improved.

DETAILED DESCRIPTION OF THE INVENTION

Figure 1:
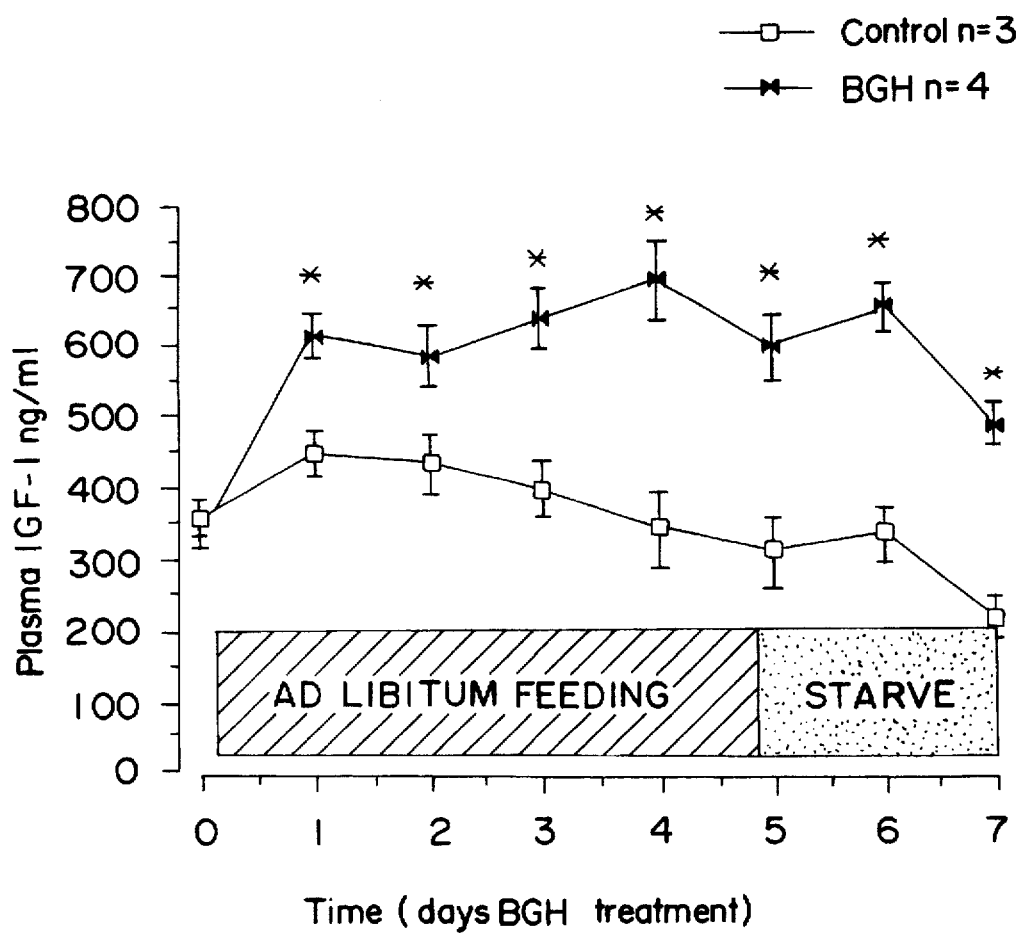

The following figures are included:

FIG. 1. Plasma IGF-I concentration during growth hormone treatment

Figure 2:
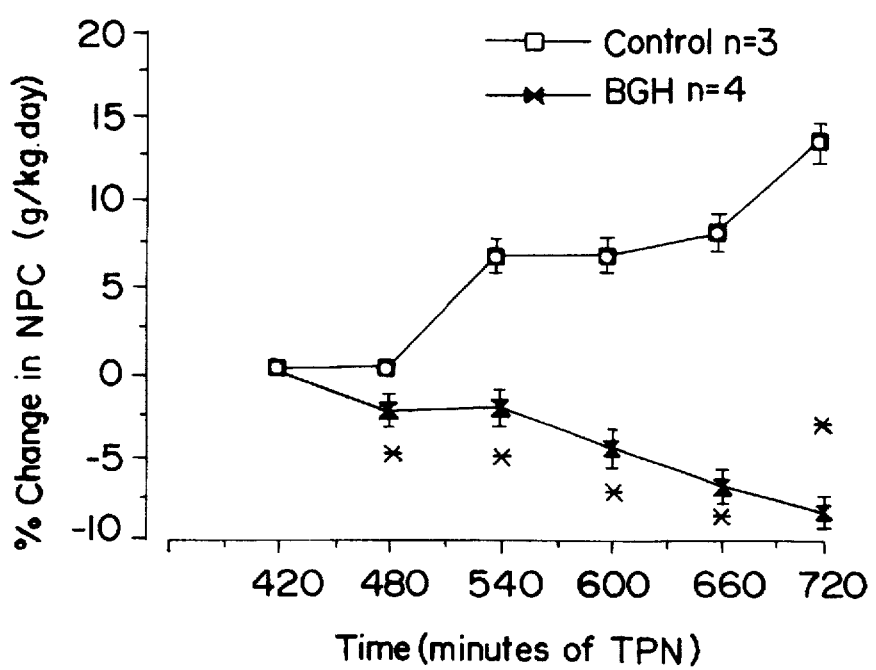

FIG. 2. The percentage change in net protein catabolism (NPC) during total parenteral nutrition (TPN).

The preferred form of the invention will now be described with reference to the following non-limiting examples.

EXAMPLE 1

Fully weaned cryptorchid ram lambs weighing 15 to 20 kg were used. The animals received once daily injections of saline (n=3) or recombinant bovine GH (n=4). Bovine GH is fully biologically active in sheep, of equal potency to ovine GH, but is the only ruminant form available as recombinant derived hormone. The bovine GH was donated by Dr I. Hart of American Cyanamid, Princeton N.J. For the first 5 days of treatment they were feed ad libitum. For the next two days they were starved to induce a catabolic state. Following 48 hours of starvation the animals were placed in slings and intravenous catheters inserted for the infusion of parenteral nutrition and the study of net protein catabolism.

FIG. 1 shows plasma IGF-1 levels through the first two phases of the experiment. It shows that pretreatment bovine GH elevated plasma IGF-1 with reference to the control group both before and during starvation. Whereas in starvation in the saline group IGF-1 fell with reference to baseline, in the GH treated group IGF-1 levels remained above basal levels. (*=p<0.05 with respect to the equivalent control value; BGH=bovine growth hormone).

Commencing at 48 hours into starvation the animals received a constant infusion of parenteral nutrition for 12 hours comprising a balanced amino acid solution (synthamin 17, Travenol) at 1.5 g/kg/day. Non protein calories were provided as a 50:50 mix of dextrose and intralipid 20 (Kabi Pharmacia) at 20 kcal/kg/day. 4 hours after commencing the parenteral nutrition, a primed constant infusion of both stable and radioisotopes was commenced. Isotopic steady state was reached 3 hours later. The isotopic infusion was of $N^{15}$ urea infused at a rate of 10 ug/kg.min after a priming dose of 4.5 mg/kg. The technique is as published and enables calculation of net protein catabolism from the measurement of urea production. At the same time $C^{14}$ leucine was infused at 7.5 nCi/kg/min following a 60.1 leucine prime as described previously. This enables calculation of whole body protein catabolism—a measure of absolute protein catabolic rate.

The net protein catabolism (NPC) at the point of first measurement was less (p<0.01) in the GH treated group than in the saline group (2.4±(SEM)0.2 g/kg/day versus 3.2 gm/kg/day). Further whereas in the saline treated group the animals continued to become more catabolic (p<0.05) despite the 5 hours further parenteral nutrition, in the GH treated group, the rate of protein catabolism decreased (p<0.05) during this period (FIG. 2). ( BGH=bovine growth hormone).

The rate of whole body protein catabolism was calculated from the leucine production rate. After 7 hours of parenteral nutrition the whole body catabolic rate was decreased (p<0.05) in the GH treated group (10.89±0.34 g/kg/day) compared to the saline group (12.87±0.67 g/kg/day).

This experiment shows that 5 days of treatment with GH commencing prior to the imposition of a catabolic stress elevates IGF-1 levels which are maintained at higher levels during the period of catabolism. Further with the continuation of the GH into the starvation period there was an unequivocal reduction in both whole body and net protein catabolism. Further whereas nutritional therapy did not alone reverse the catabolic state, when combined with GH which commenced prior to the catabolic illness, it did so.

Because this experiment does not unequivocally separate GH therapy given prior to the imposition of the stress from that given after, the experiment in example 2 was performed using human GH.

EXAMPLE 2

20 kg cryptorchid lambs were acclimatised to laboratory conditions. They were treated for 7 days with recombinant human GH (Kabi Pharmacia) or placebo at a dose of 0.5 mg/kg body weight and day divided into two doses subcutaneously. The lambs were then starved for 48 hours to mimic a catabolic stress. During the 48 hours of catabolism they were either treated with placebo or human GH at a dosing regime comparable to that used in the precatabolism phase. After 48 hours the lambs were placed in slings, percutaneously catheters were inserted in the jugular veins and a primed isotopic infusion of $C^{14}$-urea commenced at a rate of 1.8 nCi/kg/min 450:1 priming dose. Isotopic steady state was achieved after 3 hours and urea turnover rate was calculated after 5 hours further infusion. From urea turnover, net protein catabolism was calculated mathematically as described previously (Shaw J. H. F., Wolfe R. R. Glucose, fatty acid and urea kinetics in patients with severe pancreatitis. Ann. Surg. 204, 665–672, 1986). Table 1 describes the results of the study.

TABLE 1

| Group number | Precatabolism therapy | during catabolism therapy | net protein catabolism g/kg/day |
|---|---|---|---|
| A 4 | placebo | placebo | 2.59 ± 0.07 |
| B 3 | placebo | hGH | 2.76 ± 0.43 |
| C 3 | hGH | placebo | 2.75 ± 0.10 |
| D 3 | hGH | hGH | 1.92 ± 0.12* |

Data are expressed in table 1 as mean±SEM. *p<0.02 versus other groups

This example shows that hGH given prior to a catabolic stress in sheets acts synergistically with post catabolic management to reduce net protein catabolism.

EXAMPLE 3

20 kg cryptorchid lambs were acclimatised to laboratory conditions. They were treated for four days with recombinant bGH or placebo (saline) at a dose of 0.3 mg/kg body weight daily divided in two doses per day, i.e. eight injections before starvation. The lambs were starved during 70 hours and were given six injections (both saline and bGH) after initiating starvation. Net protein catabolism (NCC) was measured by Urea turnover and calculated as described in example 2. Table 2 gives the results of the study.

TABLE 2

| Group number | Precatabolism therapy | during catabolism therapy | net protein catabolism g/kg/day |
|---|---|---|---|
| I | placebo | placebo | 3.37 ± 0.78 |
| II | placebo | bGH | 2.16 ± 0.34* |
| III | bGH | placebo | 2.21 ± 0.41* |
| IV | bGH | hGH | 2.03 ± 0.54* |

Data are expressed in table 1 as mean±SEM. *p<0.001 versus placebo-placebo

Conclusion

The conclusion is apparent from these examples that the administration of GH prior to a catabolic stress is associated with an elevation in plasma IGF-1, is associated with reduced catabolism during the period of stress, is associated with a synergism with nutritional management of the catabolic stress. Thus it is clear that the prophylactic use of GH or its effective analogue including IGF-1 or its effective analogue will reduce the degree of catabolism present after a stress such as surgery and will act synergistically with the possible therapeutic approaches now available to management catabolic illness.

Finally it has to be understood that various other modifications and/or alterations may be made without departing from the spirit of the present invention as outlined herein.

I claim:

1. Method for preoperative treatment of patients in need of reduction of protein loss by administration of an effective amount of hormone (GH).

2. Method according to claim 1 for the preparation of a patient for surgery or other elective situation where catabolism may be induced.

3. Method according to claim 1 for the preparation of a patient for surgery or other elective situation to reduce the severity of a postoperative catabolic state.

4. Method according to claim 1 for preoperative and postoperative administration for the preparation of a patient for surgery or other elective situation where catabolism may be induced.

5. Method according to claim 1 for reducing the severity of catabolism following surgery.

6. Method according to claim 1 for improvement in outcome following surgery.

7. Method according to claim 1 in which human GH is used.

8. Method according to claim 1 in which the dose administered is 0.1 to 1 mg/kg/day.

9. The method of claim 5 wherein said surgery is selected from the group consisting of abdominal, cardiac, thoracic, neuro and orthopaedic surgery.

10. The method of claim 8 wherein said dose is 0.1 to 0.4 mg/kg/day.

11. The method of claim 1 wherein said administration is for at least 12 hours.

12. The method of claim 1 wherein said administration is for 3 to 60 days.

13. Method according to claim 8 in which human GH is used.

14. Method according to claim 10 in which human GH is used.

15. Method according to claim 11 in which human GH is used.

16. Method according to claim 12 in which human GH is used.

17. Method according to claim 2 in which human GH is used.

18. Method according to claim 3 in which human GH is used.

19. Method according to claim 4 in which human GH is used.

20. Method according to claim 5 in which human GH is used.

* * * * *